United States Patent
Wu et al.

(10) Patent No.: US 12,259,388 B2
(45) Date of Patent: Mar. 25, 2025

(54) COFILIN PHOSPHORYLATION FOR QUANTIFYING CD4 T CELL DAMAGE AND PREDICT CD4 T CELL RECOVERY FROM ANTI-RETROVIRAL THERAPY

(71) Applicant: VIRONGY L.L.C., Manassas, VA (US)

(72) Inventors: Yuntao Wu, Manassas, VA (US); Hong Shang, Manassas, VA (US); Yajing Fu, Manassas, VA (US)

(73) Assignee: VIRONGY L.L.C., Manassas, VA (US)

( * ) Notice: Subject to any disclaimer, the term of this patent is extended or adjusted under 35 U.S.C. 154(b) by 972 days.

(21) Appl. No.: 16/963,908

(22) PCT Filed: Jan. 23, 2019

(86) PCT No.: PCT/US2019/014756
§ 371 (c)(1),
(2) Date: Jul. 22, 2020

(87) PCT Pub. No.: WO2019/147678
PCT Pub. Date: Aug. 1, 2019

(65) Prior Publication Data
US 2021/0041437 A1 Feb. 11, 2021

Related U.S. Application Data

(60) Provisional application No. 62/620,598, filed on Jan. 23, 2018.

(51) Int. Cl.
*A61P 31/18* (2006.01)
*A61K 31/35* (2006.01)
*G01N 33/569* (2006.01)
*G01N 33/574* (2006.01)

(52) U.S. Cl.
CPC ....... *G01N 33/56972* (2013.01); *A61K 31/35* (2013.01); *A61P 31/18* (2018.01); *G01N 33/57496* (2013.01); *G01N 2333/16* (2013.01); *G01N 2333/4712* (2013.01); *G01N 2440/14* (2013.01)

(58) Field of Classification Search
CPC ........... A61P 31/18; A61P 35/00; A61K 31/35
See application file for complete search history.

(56) References Cited

U.S. PATENT DOCUMENTS

| | | | |
|---|---|---|---|
| 7,662,547 B2 * | 2/2010 | Wu | A61K 31/553 435/4 |
| 9,182,385 B2 | 11/2015 | Fant et al. | |
| 11,377,499 B2 * | 7/2022 | Wu | C07K 16/2839 |
| 2008/0064026 A1 * | 3/2008 | Wu | C12Q 1/42 435/5 |
| 2010/0292181 A1 | 11/2010 | Wu et al. | |
| 2015/0104442 A1 * | 4/2015 | Condeelis | G01N 33/57415 435/7.1 |

FOREIGN PATENT DOCUMENTS

| | | | | |
|---|---|---|---|---|
| CN | 100479863 C | | 4/2009 | |
| EP | 551200 A1 * | | 7/1993 | ............. A61K 31/35 |
| WO | 2017201187 A1 | | 11/2017 | |

OTHER PUBLICATIONS

Nebl et al., "Dephosphorylation of Serine 3 Regulates Nuclear Translocation of Cofilin", 1996, The Journal of Biological Chemistry, vol. 271, No. 42, pp. 26276-26280 . (Year: 1996).*
Gabriele Nebl et al., "Dephosphorylation of Serine 3 Regulates Nuclear Translocation of Cofilin," Journal of Biological Chemistry, Oct. 18, 1996, pp. 26,276-26,280, vol. 271, No. 42.
International Search Report & Written Opinion for PCT/US2019/014756, mailed Apr. 15, 2019.
Office Action for related China Application No. 201980021637.X, mailed Aug. 1, 2023.
Wang Yang et al., "Research progress of cofilin in diseases," Chinese Bulletin of Life Sciences, Apr. 2017, vol. 29, No. 4.
Second Office Action for China Application No. 201980021637.X, mailed Apr. 29, 2024.
Yang Dongliang et al., Immunology of Infection, Bright Belt, Leaf Blake, Lake Science and Technology, p. 335, Dec. 31, 1998. (see p. 5 of the translation for 2d SIPO Office action).
Office action in related SIPO Application No. 201980021637.X, mailed Oct. 22, 2024.

* cited by examiner

*Primary Examiner* — Michael B. Pallay
(74) *Attorney, Agent, or Firm* — Pilloff Passino & Cosenza LLP; Rachel Pilloff; Sean Passino

(57) ABSTRACT

A major immune dysfunction persisting in chronic diseases such as HIV infection and cancer is the impairment of T cell motility and migration to tissues. Therapeutics such as antiretroviral therapy or cancer therapy frequently do not fully restore T cell motility for tissue migration and infiltration. Cofilin is an actin-depolymerizing factor that regulates actin dynamics for T cell migration. Here we demonstrate that the levels of cofilin phosphorylation in blood T cells (CD4 or CD8), macrophages, B cells, natural killer (NK) cells, and/or cancer cells can be used to quantify the immune damages caused by chronic viral infection and cancer, and to predict the recovery of T cells following treatment.

2 Claims, 7 Drawing Sheets

FIG. 6

Table 1. Characteristics of clinical study participants

|  | HIV | HIV+ART | HC | P Value |
|---|---|---|---|---|
| No. of participants | 98 | 95 | 100 | — |
| Han ethnicity, no. (%) | 98 (100) | 95 (100) | 100 (100) | — |
| Male sex, no. (%) | 98 (100) | 95 (100) | 100 (100) | — |
| Age, mean (SD), years | 36 (10) | 37 (11) | 34 (11) | 0.167 |
| CD4 counts, mean (SD), cells/µl | 361 (196) | 378 (141) | — | 0.476 |
| Viral load, mean (SD), log copies/ml | 4.49 (0.71) | 0.90 (0.87) | — | <0.001 |

FIG. 7

Table 2. Patient enrollment and grouping

| HIV<br>n = 98 | | | | HIV + ART<br>n = 95 | | | HC<br>n = 100 |
|---|---|---|---|---|---|---|---|
| Reverse Phase Protein Microarray profiling of p-cofilin in blood CD4 T cells (RPPA) | | | | | | | |
| n = 33<br>No ART | n = 65<br>Received ART following RPPA | | | | | | |
| | n = 16<br>Meet criteria<br>IR | n = 26<br>Meet criteria<br>INR | n = 23<br>Do not meet<br>criteria | n = 9<br>Meet criteria<br>IR | n = 26<br>Meet criteria<br>INR | n = 60<br>Do not meet<br>criteria | | n = the number of participants; IR = Immune responder; INR = Immune

COFILIN PHOSPHORYLATION FOR QUANTIFYING CD4 T CELL DAMAGE AND PREDICT CD4 T CELL RECOVERY FROM ANTI-RETROVIRAL THERAPY

CROSS-REFERENCE TO RELATED APPLICATION

This application claims the benefit of priority of U.S. Provisional Application No. 62/620,598, filed Jan. 23, 2018, the contents of which are incorporated by reference in its entirety.

INTRODUCTION

Antiretroviral therapy (ART) has significantly extended the lifespan of HIV-infected people, but it offers neither a cure nor full immune restoration. The natural course of HIV infection leads to multiple CD4 T cell defects (1), including the impairment of T cell migration and homing to lymphoid tissues such as GALT (Gut-Associated Lymphoid Tissues) (2-4). Even with near-complete viral suppression with ART, normal levels of CD4 T cell repopulation to lymphoid tissues are rarely achieved (2, 3, 5, 6), thereby dampening immune responses and preventing full immune reconstitution for lasting viremia control (7). In HIV-infected patients, the vast majority of circulating CD4 T cells are not HIV-infected (0.2-16.4 HIV+ cells per million) (8). Thus, the T cell migratory defect seen in patients likely results from a bystander effect from chronic stimulation and receptor signaling by viral (9, 10) and/or inflammatory factors (1, 2). However, the molecular mechanism dictating this persistent T cell dysfunction had not been fully elucidated. This has hindered the development of an effective therapy to restore T cell functions, and to achieve persistent immune control and clearance of HIV.

In cancers, there is also a similar impairment of T cell migration and infiltration into tumors (11). T cells such as CD8 T cells play a critical role in cancer immunity, but tumors can use various defense mechanisms, either directly or indirectly, to inhibit T migration to tumor bed for immune control (11).

In the human immune system, T cell activity is mainly regulated by receptor signaling. Persistent stimulation and signaling through chemotactic receptors (e.g., chemokine receptors, cytokine receptors, integrin receptors, adhesion molecule receptors, and co-stimulatory molecule receptors such as CD28, CTLA-4, and PD-1/PD-L) frequently leads to T cell polarization and commitment to distinct lineages. In HIV infection, the virus infects T cells through gp120 binding to CD4 and the chemokine co-receptor CXCR4 (X4) or CCR5 (R5) (12, 13). Such binding also initiates aberrant signaling and has pathogenic consequences (9, 10, 14, 15). In particular, HIV signaling through CXCR4 has been shown to activate an actin depolymerizing factor, cofilin, to promote the actin dynamics necessary for viral nuclear entry in blood resting CD4 T cells (9, 16). Similarly, in other chronic diseases such as cancer, the persistent stimulation of immune cells by high levels of inflammatory chemokines, such as IP-10 (17, 18), and tumor antigens can also cause T polarization and dysfunction, and impair T cell motility (FIG. 1)

A major cellular protein controlling T cell motility and migration is cofilin. Cofilin is an actin-binding protein, one of the membranes of the ADF/cofilin family proteins ubiquitously present among eukaryotes. ADF/cofilin proteins bind and depolymerize filamentous F-actin in a pH-dependent manner and are responsible for the high turnover rates of actin filaments in cells. The first member of the ADF/cofilin family proteins was identified in extracts of embryonic chick brain (19). Cofilin was later purified from porcine brain and named cofilamentous structures with actin, or cofilin for short. Currently, there are three highly conserved proteins in the ADF/cofilin family: ADF (actin depolymerizing factor) or destrin, cofilin 1 (non-muscle cofilin or cofilin), and cofilin-2 (muscle-cofilin). Cloned human cofilin has 166 amino acids and a deduced molecular weight of 18 kD (20).

Structurally, human cofilin possesses a core consisting of a five-stranded mixed β-sheet (β1 to β5). The first four strands (β1 to β4) are anti-parallel, and β5 runs parallel to β4 and anti-parallel to β3. In addition, the residues 159-161 at the C-terminal form a short stand, β6. Five helices (α1 to α5) surround the central β-sheet, and a salt bridge is formed between $His^{133}$ and $Asp^{98}$ that may influence the pH sensitivity of cofilin in actin binding and depolymerization. Cofilin binds to G actin, and the binding site is located in a region centered around $Tyr^{117}$, which includes several residues in α4 (such as $Lys^{112}$, $Lys^{114}$, $Met^{115}$, and $Ile^{124}$) and β5. In addition, a few other residues such as $Ile^{12}$, $Pro^{110}$ and $Leu^{128}$ are also suggested in G-actin binding. Cofilin also binds to F-actin, and this requires two sites on cofilin, a G site that interacts with actin subdomains 1 and 3 and an F site that interacts with actin subdomains 1 and 2. Residues important for F-actin binding on cofilin have been identified through mutagenesis and include several residues in β4 (such as $Lys^{96}$ and $Asp^{98}$) and α5 (such as $Glu^{151}$, $Lys^{152}$, and $Gly^{155}$). Other regions including β3 and β5 may additionally be involved in F-actin binding (21).

Cofilin depolymerizes actin filaments through two mechanisms: direct severing and increasing the off-rate of actin subunits from the (−) end (22, 23). Cofilin has a higher affinity for ADP-actin than for ATP-actin, and cofilin binding to actin filaments facilitates phosphate dissociation from ATP-actin. Hydrolysis of ATP increases cofilin binding affinity, changing the twist of the actin helix and severing actin filaments to shorter segments (24). These severed actin filaments can increase the speed of actin polymerization by providing more free (+) ends for nucleation by the Arp2/3 complex (25).

The binding of cofilin to ADP-actin present at the (−) end also promotes dissociation of cofilin-ADP-actin. Cofilin in the released ADP-actin complex is competitively replaced by profilin, which then coverts ADP-actin monomers to ATP-actin monomers to recycle them for new actin polymerization at the (+) end. Thus, it is suggested that cofilin and the Arp2/3 complex work together to regulate actin treadmilling, in which ATP-actin is preferentially incorporated into the filaments through Arp2/3 at the (+) end, and then hydrolyzed into "older" ADP-actin and dissociated from the (−) end by cofilin (23, 26).

In cells, the activity of cofilin is mainly regulated by phosphorylation of serine 3 at the N-terminal, which inhibits cofilin binding to G-actin and F-actin. The kinases responsible for cofilin serine 3 phosphorylation are the LIM domain kinases (LIMK) and Tes kinases, which are targets of the Rho family GTPases such as Rho, Rac, and Cdc42 (27). Rho family GTPases activate PAK1, PAK2, PAK4, ROCK, or MRCKα (myotonic dystrophy kinase-related Cdc42-binding protein kinase) which then activate LIMK through direct phosphorylation. Cofilin is activated through dephosphorylation of serine 3 by phosphatases such as PP1, PP2A, slingshot IL (SSH1L), and chronophin, which couple cofilin activity to different signal pathways (28-30). Recent studies have suggested that tyrosine 68 (Y68) can also be phosphorylated, and this phosphorylation appears to increase cofilin ubiquitination and proteasome degradation (31). In chemotactic cells, cycles of cofilin phosphorylation and dephosphorylation are required to sustain the actin dynamics essential for driving directional cell migration.

In cells, cofilin is a key regulator of actin dynamics and is also involved in multiple cellular processes (32). The ability of cofilin to modulate actin polymerization or depolymerization may depend on the local concentration of cofilin. Low concentrations of cofilin favor severing, whereas high concentrations favor actin nucleation. Nevertheless, it is unknown how this concentration-dependent mode of action demonstrated in test tubes plays out in cells (33). In general, decreasing cofilin expression through siRNA increases the amounts of cellular actin filaments, whereas over-expression of cofilin induces the formation of cofilin-actin bundles (9). In vitro, cofilin also competitively interacts with the Arp2/3 complex by inducing structural changes in the actin filaments; these changes reduce the affinity for Arp2/3 and cause a loss of actin filament branches. This debranching process may play a role in modulating Arp2/3-induced actin branch growth in the leading edge of migrating cells (34).

In addition to regulating actin dynamics in cells, cofilin has also been shown to mediate actin nuclear localization, which may be involved in the regulation of gene expression. Actin and actin-related proteins such as Arp7, Arp9, and Baf53 are parts of the chromatin-remodeling complex RSC and SWI/SNF (35, 36). Actin is also part of the pre-initiation complexes and is necessary for transcription by RNA polymerase II (37). Cofilin-mediated actin nuclear localization may serve to connect the cytoskeletal processes to chromatin remodeling and the initiation of transcription.

Cofilin serine 3 phosphorylation inactivates the actin binding ability of cofilin. However, phospho-cofilin is recently shown to activate phospholipase D1 (PLD1). Cofilin directly and specifically interacts with PLD1 upon phosphorylation by LIMK1. Phospho-cofilin also stimulates PLD1 activity, suggesting that phospho-cofilin may control a variety of cellular functions by its stimulatory effect on PLD1 (38).

In the human immune system, cofilin plays important roles in regulating T cell migration, chemotaxis, and T cell activation. Within the immunological synapse, cofilin is required for the formation of the supramolecular activation clusters critical for sustaining signaling and T cell activation. Cell-permeable peptides that block cofilin interaction with F-actin impair receptor capping and immunological synapse formation, resulting in inhibition of T cell activation (39). In human blood resting T cells, in the absence of T cell activation or chemotactic stimulation, cofilin exists largely as the serine 3 phosphorylated form. T cell activation or chemotactic stimulation leads to transient cofilin activation by dephosphorylation, and the signaling cascade is mainly transduced through costimulatory receptors such as CD2, CD28, and the chemokine receptors such as CXCR4. While TCR/CD3 stimulation activates the Arp2/3 complex for actin polymerization, CD28-mediated costimulation triggers cofilin activation, which is required for dynamic actin reorganization and sustaining T cell signaling (40). The GTPase Ras and PI3K (phosphatidylinositol-3-kinase) signaling cascade is suggested to mainly regulate dephosphorylation of cofilin in unstimulated human blood T cells (41). Inhibition of either MAPK/ERK kinase or PI3K blocks Ras-induced and costimulation-induced cofilin dephosphorylation, whereas transient expression of a dominant negative form of H-Ras inhibits PI3K activation and cofilin dephosphorylation (41).

In HIV infection, the virus enters into cells through binding to CD4 and the chemokine coreceptor, CXCR4 or CCR5. During this entry process, HIV-1 binding to CXCR4 also triggers a transient course of cofilin phosphorylation and dephosphorylation to increase actin dynamics in resting CD4 T cells (9, 42). It is suggested that the cortical actin in resting T cells is relatively static in the absence of T cell activation or chemotactic stimulation. This lack of actin activity limits viral early processes such as entry, DNA synthesis, and nuclear migration (9). Cofilin increases cortical actin dynamics and actin treadmilling, facilitating viral intracellular migration towards the nucleus (9). Cofilin and actin-mediated HIV nuclear localization is suggested to be essential for the establishment of HIV-1 latency in resting CD4 T cells (9, 16). Slight inhibition of cofilin expression through siRNA knockdown increases cortical actin density, which leads to an increase in HIV DNA synthesis but a decrease in the amounts of HIV-1 nuclear DNA and early transcripts (9). Induction of cofilin activity using a human cofilin-derived peptide (S3) carrying the N-terminal 16 residues competitively inhibits cofilin phosphorylation through LIMK1, and this induction enhances HIV latent infection of resting CD4 T cells. A pharmacological drug, staurosporine, is also shown to induce gradual cofilin activation that enhances HIV latent infection of resting CD4 T cells following a transient treatment during infection (9). In addition, pre-treatment of resting CD4 T cells with chemokines such as CCL19, CXCL9, CXCL10, and CCL20 lead to cofilin activation and changes in actin filaments which greatly promote HIV nuclear migration and DNA integration (16, 43). Interestingly, exposing cells to mechanical shear stress, such as infecting cells under conditions of low speed spinning or spinoculation, also triggers cofilin activation and actin dynamics, resulting in the upregulation of CXCR4 and a great enhancement of HIV-1 DNA synthesis and nuclear migration (44).

HIV-1-mediated cofilin activation in resting CD4 T cells is shown to be through the Gαi-dependent signaling from CXCR4; pertussis toxin (PTX), a bacterial toxin inhibiting G-protein-coupled receptors by the ADP-ribosylation of Gαi, inhibits cofilin activation and HIV-1 latent infection of resting T cells (9). Cofilin can be phosphorylated by LIMK, and HIV-1 binding to blood CD4 T cells and macrophages triggers rapid activation of LIMK1, coincident with HIV-mediated early actin polymerization in T cells (42). It is suggested that HIV-1 hijacks LIMK1/cofilin activity to directly regulate actin and CXCR4 dynamics critical for viral entry, postentry DNA synthesis, and nuclear migration. Inhibition of LIMK1 activity through siRNA knockdown decreases filamentous actin and T cell chemotaxis towards SDF-1. The decrease in cortical actin density also leads to an increase in CXCR4 internalization and surface recycling. Thus, LIMK-mediated early cortical actin polymerization may result in a temporary block to CXCR4 internalization, facilitating viral fusion and CXCR4 signaling. The LIMK1 knockdown cells also support lower viral entry, DNA synthesis, and nuclear migration. In addition, transient treatment of resting CD4 T cells with a pharmacological agent, okadaic acid, activates LIMK and promotes HIV latent infection of resting CD4 T cells. The signaling pathway that mediates LIMK activation by HIV-1 is identified as the Rac1, PAK1/2 and LIMK pathway in blood resting T cells. The activation is likely triggered by gp120 signaling through both CD4 and CXCR4, as well as from both Gαi and Gαq (42). In transformed cancer cells, HIV binding to CD4 and CXCR4 is also suggested to trigger filamin A activation which then leads to RhoA-ROCK-LIMK activation. This activity is proposed to permit F-actin reorganization for receptor clustering (45). HIV gp120-mediated cofilin phosphorylation is also suggested to inhibit T cell chemotaxis towards SDF-1 (46).

In addition to HIV-1 gp120, another HIV pathogenic factor, Nef, is also suggested to regulate cofilin activity (47). Over-expression of Nef in a human cancer Jurkat T cell inhibits SDF-1-induced membrane ruffling, actin rearrangement, and cell migration towards CXCL12, CCL3, and CCL19 (47, 48). Over-expression of Nef in hamster CHO cells also inhibits wounding-induced cofilin activation in a cell wound healing assay. It has been suggested that the Nef-PAK2 complex is involved in the phosphorylation of cofilin, although Nef does not appear to alter the activity of PAK2 in an in vitro cofilin phosphorylation assay. Functionally, Nef-mediated cofilin dysregulation may affect migratory behavior of infected T cells (47).

SUMMARY

Provided herein are methodology, compositions, kits, and the like for determining the levels of cofilin phosphorylation in blood T cells (CD4 or CD8), which can be used to quantify the immune damages caused by chronic viral infection and cancer, and to predict the recovery of T cells following treatment. Based on this determination of a correlation between cofilin phosphorylation and immune dysfunction, suitable patients may be treated with a composition that causes cofilin dysregulation and restores cofilin phosphorylation.

For instance, and in no way limiting, levels of cofilin phosphorylation in HIV-infected patients can be used as a marker to quantify immune dysfunction and damages by the virus.

In another embodiment, levels of cofilin phosphorylation in HIV-infected patients can be used to measure drug effects on immune function (ART and other immune modulating drugs). Levels of cofilin phosphorylation in HIV-infected patients can be used to predict the recovery of T cell functions from drug treatment (ART and other immune modulating drugs).

In another embodiment, levels of coflin phosphorylation in cancer cells can be used to quantify alteration in cell motility, migration, tissue infiltration, and metastasis.

In another embodiment, levels of cofilin phosphorylation in T cells (CD4/CD8) in cancer patients can be used to predict immune dysfunction in cancer, and predict drugs effects in restoring anti-tumor immunity.

In some embodiments, a method for detecting and treating immune dysfunction in a patient comprises (a) quantifying cofilin phosphorylation levels in T cells (CD4/CD8), monocytes/macrophages, B cells, natural killer (NK) cells, and/or cancer cells of said patient, wherein said patient with immune dysfunction has lower or higher cofilin phosphorylation levels than a control healthy person or patient; and (b) administering to said patient an effective amount of a composition that corrects cofilin dysregulation and restores cofilin phosphorylation.

In some embodiments, the patient has a chronic disease causing immune dysfunction. In some embodiments, the said chronic disease is HIV infection or cancer.

In some embodiments, said immune dysfunction is aberrant T cell, macrophage, B cell, NK cell activation, impairment of T cell, monocyte/macrophage, B cell, NK cell motility and/or tissue migration.

In some embodiments, the composition is a cofilin phosphatase inhibitor or cofilin kinase activator. In some embodiments, the composition comprises okadaic acid.

In some embodiments, a method for determining immune dysfunction in a patient, comprises quantifying cofilin phosphorylation in T cells (CD4/CD8), monocyte/macrophages, B cells, natural killer cells, and/or cancer cells in said patient.

In some embodiments, the patient is a cancer patient or HIV-infected patient.

In some embodiments, the method for treating cancer in a patient comprises (a) quantifying cofilin phosphorylation levels in T cells (CD4/CD8), monocyte/macrophages, B cells, natural killer cells, and/or cancer cells of said patient, wherein said patient has lower or higher cofilin phosphorylation levels than a control healthy person; and (b) administering to said patient an effective amount of a composition that restores cofilin phosphorylation.

In some embodiments, the composition is a cofilin phosphatase inhibitor or cofilin kinase activator or an antibody against chemotactic receptors that can trigger cofilin phosphorylation or dephosphorylation or a small molecule that can trigger cofilin phosphorylation or dephosphorylation. In some embodiments, the composition comprises okadaic acid.

In some embodiments, the method is for treating a patient having cancer, including, for example, patients who do not have HIV or AIDS.

BRIEF DESCRIPTION OF THE FIGURES

FIG. 6. Characteristics of clinical study participants. Details are in examples.

FIG. 7. Patient enrollment and grouping. Details are in examples.

DETAILED DESCRIPTION

Figure 1:
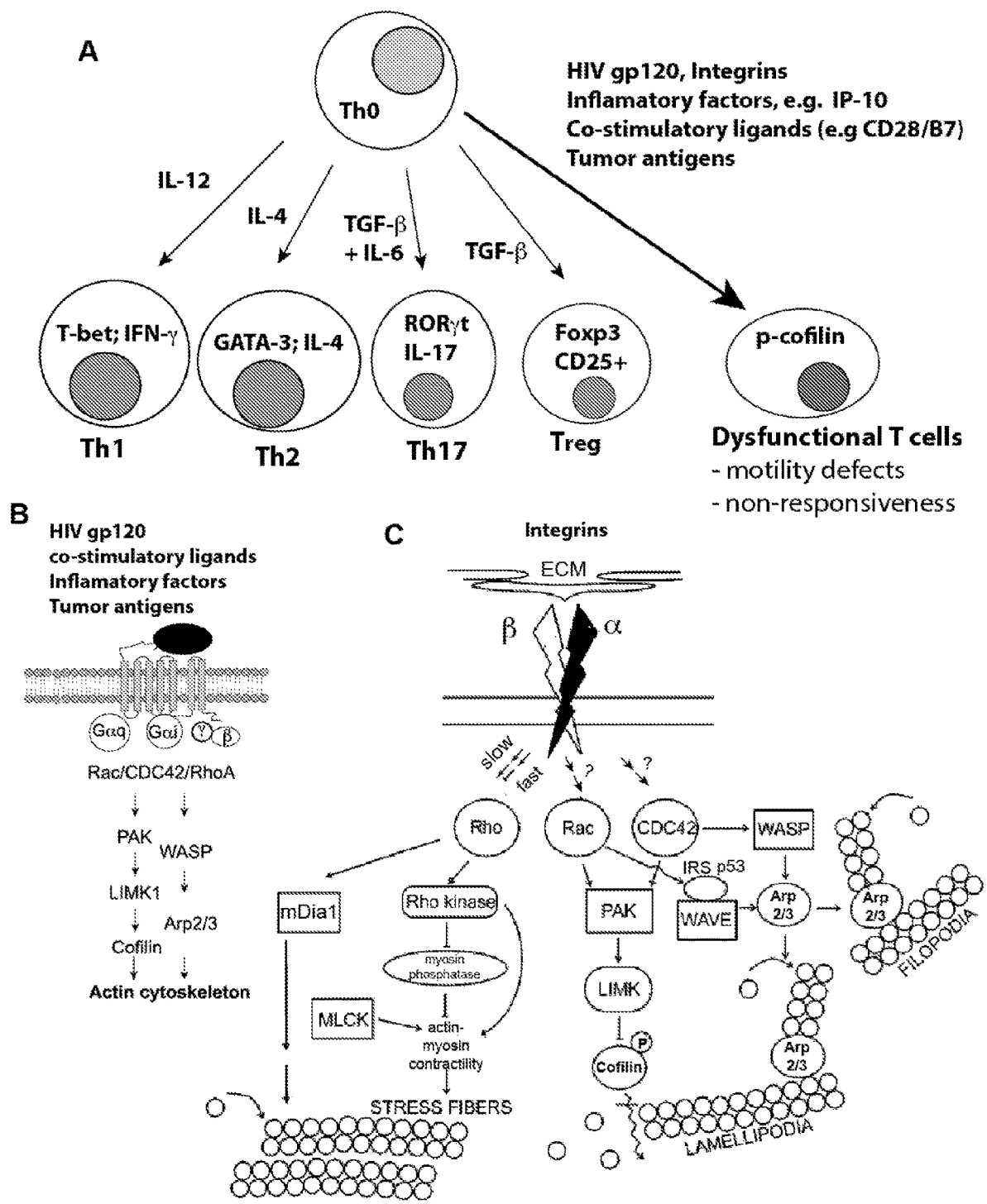
FIG. 1. Persistent stimulation of T cell surface receptors can lead to T cell polarization to different lineages. (A) Persistent and chronic stimulation of chemotactic receptors (e.g., chemokine receptors, cytokine receptors, integrin receptors, adhesion molecule receptors, and co-stimulatory molecule receptors, such as CD28/B7, B7-2, CTLA-4/B7, B7-2, and PD-1/PD-L) can leads to T cell polarization and commitment to distinct lineages, such as an irreversible pathogenic lineage with chronic cofilin hyperactivation. (B) The signaling pathways involved in cofilin activation through the stimulation of receptors. (C) The signaling pathways involved in cofilin activation through the stimulation of integrin receptors (modified from Juliano, 2002, Annu Rev Pharmacol Toxicol 42:283).

A major immune dysfunction persisting in chronic diseases such as HIV infection and cancer is the impairment of T cell motility and migration to tissues. Therapeutics such as antiretroviral therapy or cancer therapy frequently do not fully restore T cell motility for tissue migration and infiltration. Cofilin is an actin-depolymerizing factor that regulates actin dynamics for T cell migration.

As explained below, the present inventors determined that the levels of cofilin phosphorylation in blood T cells (CD4 or CD8) can be used to quantify the immune damages caused by chronic viral infection and cancer, and to predict the recovery of T cells following treatment. Based on this determination of a correlation between cofilin phosphorylation and immune dysfunction, suitable patients may be treated with a composition that corrects cofilin dysregulation and restores cofilin phosphorylation. For example, cells can be treated with cofilin phosphatase inhibitors or cofilin kinase activator to increase cofilin phosphorylation, as demonstrated by the use of okadaic acid to increase cofilin phosphorylation (42) or an anti-integrin antibody to modulate the cofilin pathway (49).

A potential pathogenic role of HIV-1-mediated cofilin dysregulation is proposed from studies of cofilin activation in blood resting CD4 T cells treated with HIV or gp120 (50). It was shown that HIV-1 or gp120 stimulates cycles of cofilin phosphorylation and dephosphorylation, suggesting that chronic exposure of CD4 T cells to HIV or gp120 may have a lasting impact on cofilin activity and T cell functionality. A small-scale clinical study has found that in the peripheral blood of HIV-1-infected patients, levels of active cofilin in their resting CD4 T cells are significantly higher. It is suggested that HIV-1-mediated dysregulation of cofilin may lead to abnormalities in T cell migration and activation that could contribute to viral pathogenesis (50).

Given that cofilin is a major part of the motility engine in T cells, it is possible that the T cell migratory defects seen in HIV-infected patients may directly result from cofilin dysregulation by persistent, pathogenic signaling occurring during HIV infection (50). In HIV infection, during acute phase, gp120 levels are very high with active HIV replication. CD4 T cells are exposed to these high levels of gp120 for extended periods of time before ART (Antiretroviral therapy) initiation. During the asymptomatic phase with ART, gp120 in the peripheral blood is at a low level. However, in infected lymphoid tissues, gp120 can be present in high concentrations (>300 pg/ml), and is estimated to be in the range of 10 pg/ml to 10 ng/ml (51). Given that the CD4 T cells in HIV patients are chronically exposed to viral proteins such as gp120 (52), particularly during the acute phase, persistent viral signaling may trigger cofilin dysregulation and cause a T cell migratory defect, as seen in HIV patients (2, 3, 50).

A. Effects of HIV Infection on Cofilin Activity

To detect the effects of HIV infection on cofilin activity, and as explained below, the present inventors conducted a large clinical trial to examine cofilin phosphorylation in blood resting CD4 T cells (FIG. 2A). For this purpose, a reverse phase phospho-cofilin micro-array was developed that can quantify cofilin phosphorylation in a large number of clinical samples simultaneously (53) (FIG. 2B). Blood resting CD4 T cells from HIV patients, with ART (HIV+ ART, n=95) or without ART (HIV, n=98), or from healthy controls (HC, n=100) (Table 1) were purified by negative depletion, unstimulated, and then lysed. Blindly coded cell lysates were then profiled with the phospho-cofilin microarray (FIG. 2C). As shown in the figures, the inventors observed a highly significant reduction in cofilin phosphorylation in HIV patients (HIV=0.968; HIV+ART=1.139; healthy control=2.254; p<0.001). Surprisingly, ART did not significantly restore cofilin phosphorylation (HIV=0.968; HIV+ART=1.139; p=0.981). These results suggest that HIV-mediated cofilin hyperactivation may result from ART-irreversible, pathogenic polarization of T cells. This irreversibility appears to resemble the establishment of an early immune activation set point that dictates subsequent CD4 T cell depletion independent of viral load (1).

B. Cofilin Hyperactivation and Viral Load/CD4 Count

The inventors next examined possible correlations between cofilin hyperactivation and viral load/CD4 count. In untreated patients, there was only a weak correlation between cofilin phosphorylation and viral load (p=0.043, r=−0.205) (FIG. 2D), and there was no correlation between cofilin phosphorylation and CD4 T cell counts (p=0.057, r=0.193) (FIG. 2E). However, when ART-treated patients were categorized into immune responders (IR) and immune non-responders (INR), the IR had a significantly higher level of cofilin phosphorylation than the INR (FIG. 2F). Both IR and INR had the viral load suppressed to the limit of detection after one year of treatment; the INR had less than 20% recovery of CD4 T cells or a CD4 T cell count below 200, whereas the IR had greater than 20% T cell recovery and a CD4 count above 500. Thus, higher levels of p-cofilin in ART-treated patients were associated with a better CD4 T cell recovery after ART. ART-naïve patients were followed after their p-cofilin profiling. Some of these patients were subsequently treated with ART (Table 2). Again, the IR had significantly higher levels of cofilin phosphorylation than the INR (FIG. 2G). These results demonstrate that pre-ART levels of p-cofilin can be used to gauge the degree of CD4 T cell damage and predict T cell recovery from ART.

Figure 2:
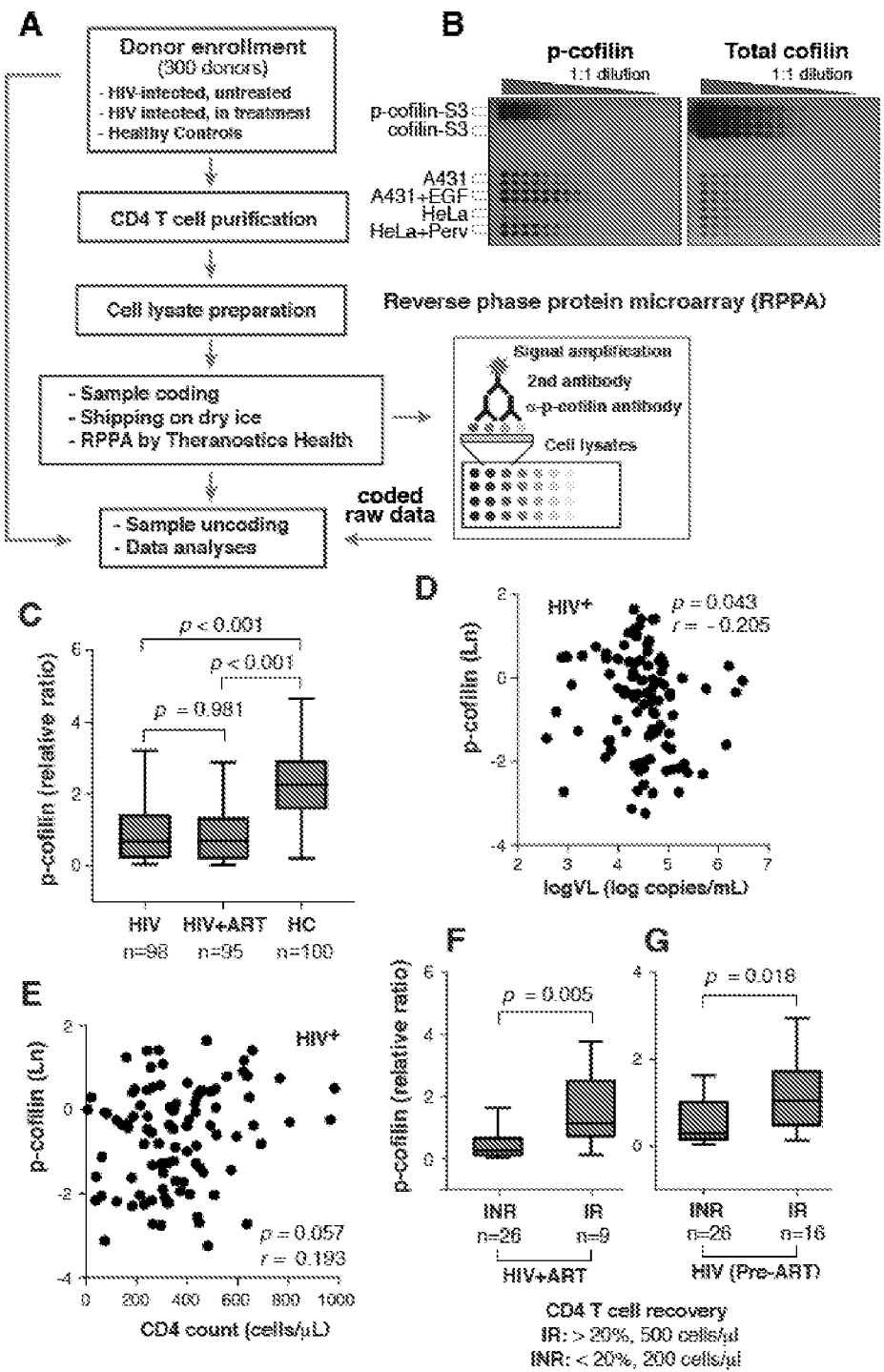
FIG. 2. Cofilin hyperactivation in HIV infection. (A) Flowchart of the clinical study. (B) Development of the reverse-phase cofilin microarray for profiling cofilin phosphorylation. Synthetic peptides or cell lysates were serially diluted (1:1) and printed onto the microarray slides, which were then stained with antibodies against either total cofilin (right) or phospho-cofilin (left). P-cofilin-S3, a synthetic cofilin peptide with serine 3 phosphorylated; cofilin-S3, a similar peptide with no serine 3 phosphorylation. A431 or HeLa cells were not treated or treated with human epithelial growth factor (EGF) or pervanadate (Perv). (C) Relative levels of p-cofilin in blood resting CD4 T cells from HIV-infected patients with ART (HIV+ART) or without ART (HIV), or healthy control donors (HC) were profiled. Box plots show interquartile range, median, and range. There were no statistically significant differences in the total protein levels of the resting CD4 T cells from HC, HIV, and HIV+ART (see Materials and Methods). (D and E) The correlation between levels of p-cofilin and plasma viral load (D) and CD4 T cell count (E) in untreated patients were plotted using Spearman rank correlation tests (Ln, natural logarithm). (F) In ART-treated patients, immune responders (IR) had significantly higher levels of cofilin phosphorylation than did non-responders (INR). (G) A subgroup of ART-naïve patients was subsequently treated with ART following p-cofilin profiling. Immune responders (IR) had significantly higher levels of cofilin phosphorylation than non-responders (INR).
Figure 3:
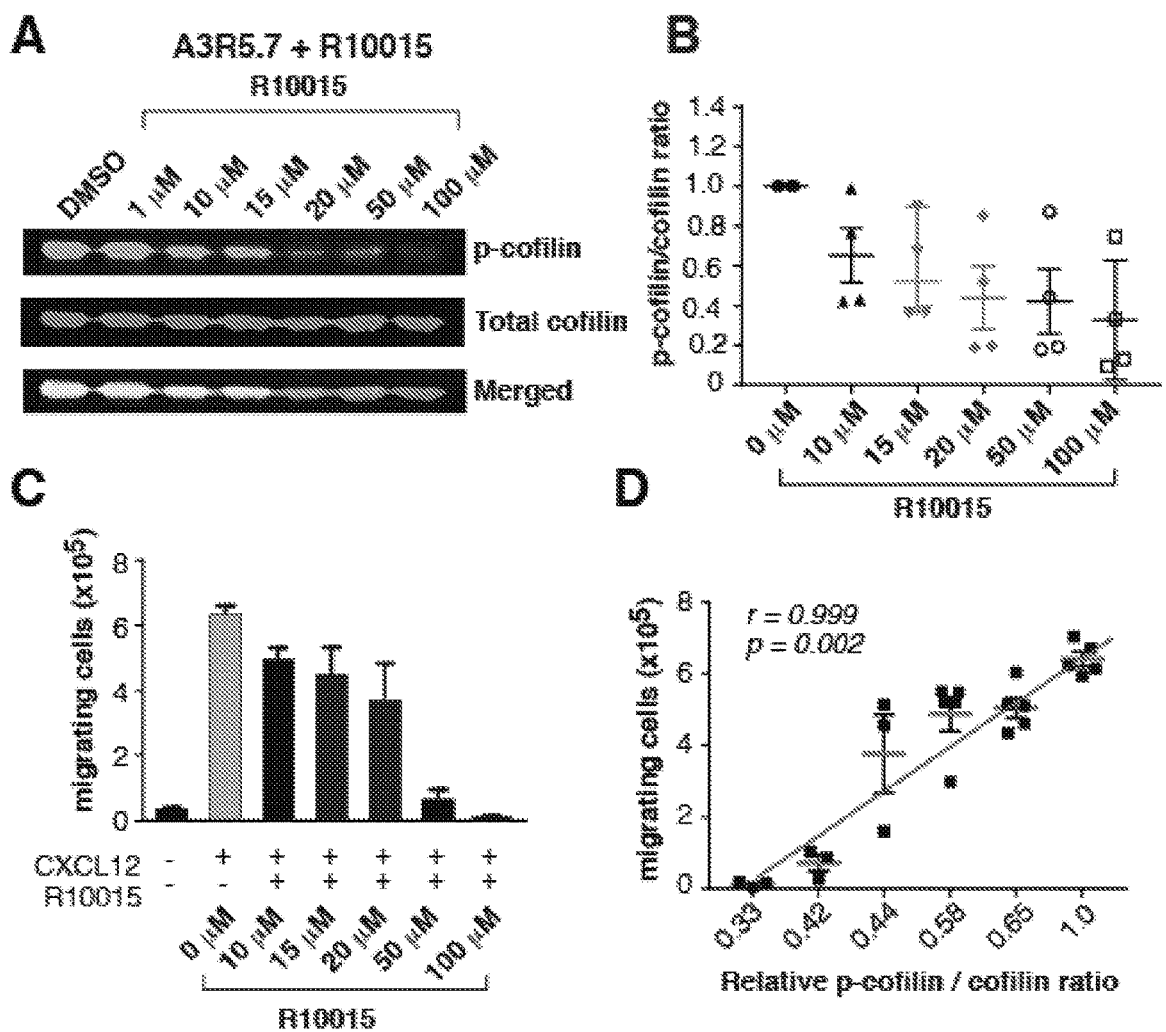
FIG. 3. Quantification of effects of cofilin hyperactivation on T cell migration. (A) A3R5.7 T cells were treated with different dosages of R10015 for one hour. Phospho-cofilin and total cofilin were quantified by Western blot. (B) The relative ratio of p-cofilin/cofilin in response to R10015 treatment was plotted (n=4 independent experiments). (C) R10015 inhibits cofilin phosphorylation and T cell chemotaxis in response to CXCL12. A3R5.7 cells were treated with different dosages of R10015 for one hour, and then added to the upper chamber of a 24-well transwell plate. The lower chamber was filled with CXCL12 (40 ng/ml), and cell migration to the lower chamber was quantified (n=3 independent experiments). (D) The linear correlation between T cell migration and levels of cofilin phosphorylation. The X-axis is the relative ratio of p-cofilin/cofilin derived from (B); the Y-axis is the number of migrating cells derived from (C).

Cofilin hyperactivation has been shown to be associated with a migratory impairment of CCR6+ and CXCR3+ helper T cells (Th), which are prevented from trafficking from the blood stream to peripheral organs even in aviremic HIV patients on long-term ART (2). T cell migration is controlled by cycles of cofilin phosphorylation and dephosphorylation, which are regulated by the LIM-domain kinase (LIMK) through serine 3 phosphorylation (27, 54). To quantify the direct effect of cofilin hyperactivation on T cell migration, we used a recently discovered LIMK inhibitor, R10015 (55), to block cofilin phosphorylation in A3R5.7 CD4 T cells. We then performed CXCL12-induced T cell chemotaxis in the presence of cofilin hyperactivation. CXCL12 (SDF-1, stromal cell-derived factor 1) binding to CXCR4 triggers actin/cofilin dynamics for T cell migration (9). We observed a R10015 dosage-dependent inhibition of cofilin phosphorylation in A3R5.7 CD4 T cells (FIGS. 3A and 3B). A linear correlation was observed between cofilin dephosphorylation and the impairment of CXCL12-mediated T cell chemotaxis (FIGS. 3C and 3D) (correlation coefficient r=0.999, p=0.002). At around 15 M of R10015, cofilin phosphorylation was reduced to around 50% in A3R5.7, a level approximate to what was seen in HIV patients (FIG. 3A and FIG. 2C). A 50% reduction in cofilin phosphorylation resulted in a 20-40% decrease in cell migration for human A3R5.7 CD4 T cells (FIG. 3C). These results quantitatively measured the direct impact of cofilin hyperactivation on T cell motility.

It has long been speculated that HIV binding to chemokine coreceptors may trigger aberrant G protein signaling and CD4 T cell pathogenesis (12). Nevertheless, this speculation has not been solidified by experimental and clinical data. In this large clinical trial, the inventors demonstrated cofilin dephosphorylation occurring in the blood CD4 T cells of HIV-infected patients. Cofilin has been identified as a direct downstream target of HIV-mediated G protein signaling through the chemokine coreceptors (9). Cofilin hyperactivation can directly affect T cell migration (40), as cofilin is a major driver of actin treadmilling for cell motility (56). In HIV infection, selective impairment of CD4 but not CD8 T cell homing (2, 4) is a major hallmark of HIV-mediated T cell dysfunction (3), and this implies a direct role of cofilin dysregulation in HIV-mediated CD4 T cell pathogenesis. The molecular cue for this cofilin hyperactivation likely results from early viral signaling from HIV gp120 (9) and chronic immune activation later in the disease course (2). It has been known that in HIV-infected patients, levels of inflammatory cytokines such as IP-10 are very high in the peripheral blood (17, 18). Thus, the combined effects of gp120 and chronic immune activation may exacerbate and polarize CD4 T cells towards an ART-irreversible pathogenic lineage. This HIV-mediated T cell polarization may resemble the irreversibility of T cell differentiation and lineage commitment following persistent cytokine receptor signaling. For example, when T cells are stimulated with IL-12 or interferon-γ for an extended period of time, they are polarized to express a transcription factor, T-bet, and the induction of which becomes irreversible. The ART-irreversibility of cofilin hyperactivation also appears to resemble the establishment of the early immune activation set point that dictates subsequent CD4 T cell dysfunction and depletion independent of viral load (1).

Figure 4:
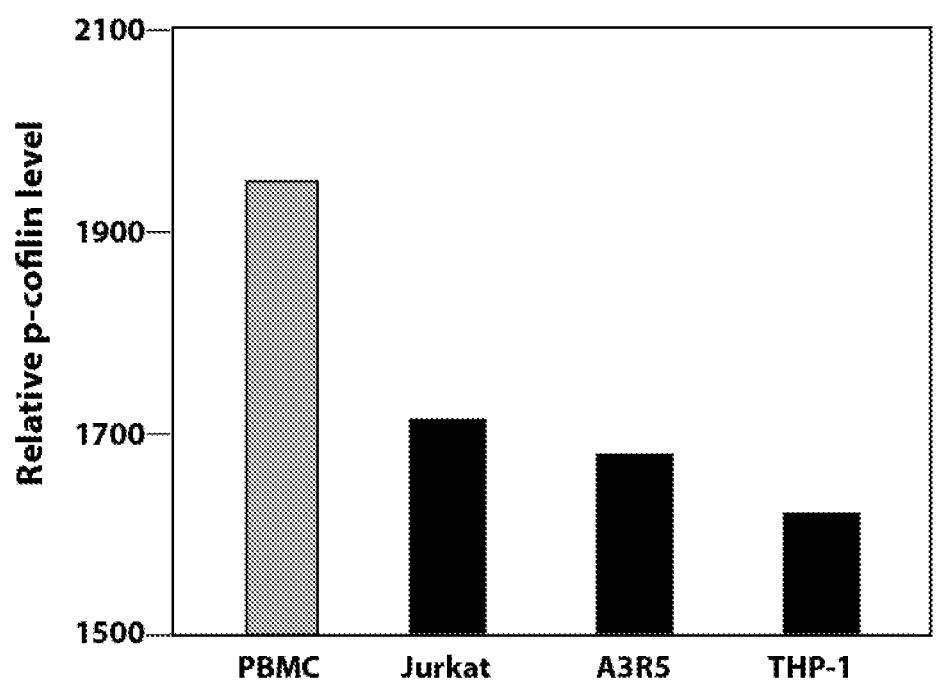
FIG. 4. Cofilin hyperactivation in blood cancer cells. Peripheral blood mononuclear cells (PBMC) from healthy donors, Jurkat cancer T lymphocyte cells (derived from a patient with acute T cell leukemia), A3R5.7 T cells (derived from the peripheral blood buffy coat of a four-year-old patient with acute lymphoblastic leukemia), or THP-1 blood monocytic cancer cells (derived from an acute monocytic leukemia patient) were fixed, permeabilized, washed, and then stained with a rabbit polyclonal anti-human p-cofilin antibody for 60 min. Cells were washed twice and stained with Alexa Fluor 488-labeled anti-rabbit antibodies. Cells were washed twice, and then analyzed by flow cytometry. The relative p-cofilin staining was calculated by using the mean fluorescent intensity from p-cofilin staining subtracting the mean fluorescent intensity from the non-specific background staining from similarly-labeled isotype control antibodies.

It was also found that similar to HIV-1-mediated cofilin hyperactivation, human cancer cells also carry lower-levels of cofilin phosphorylation (FIG. 4), demonstrating the motility of transformed cancer cells have been fundamentally altered through changing cofilin phosphorylation.

Figure 5:
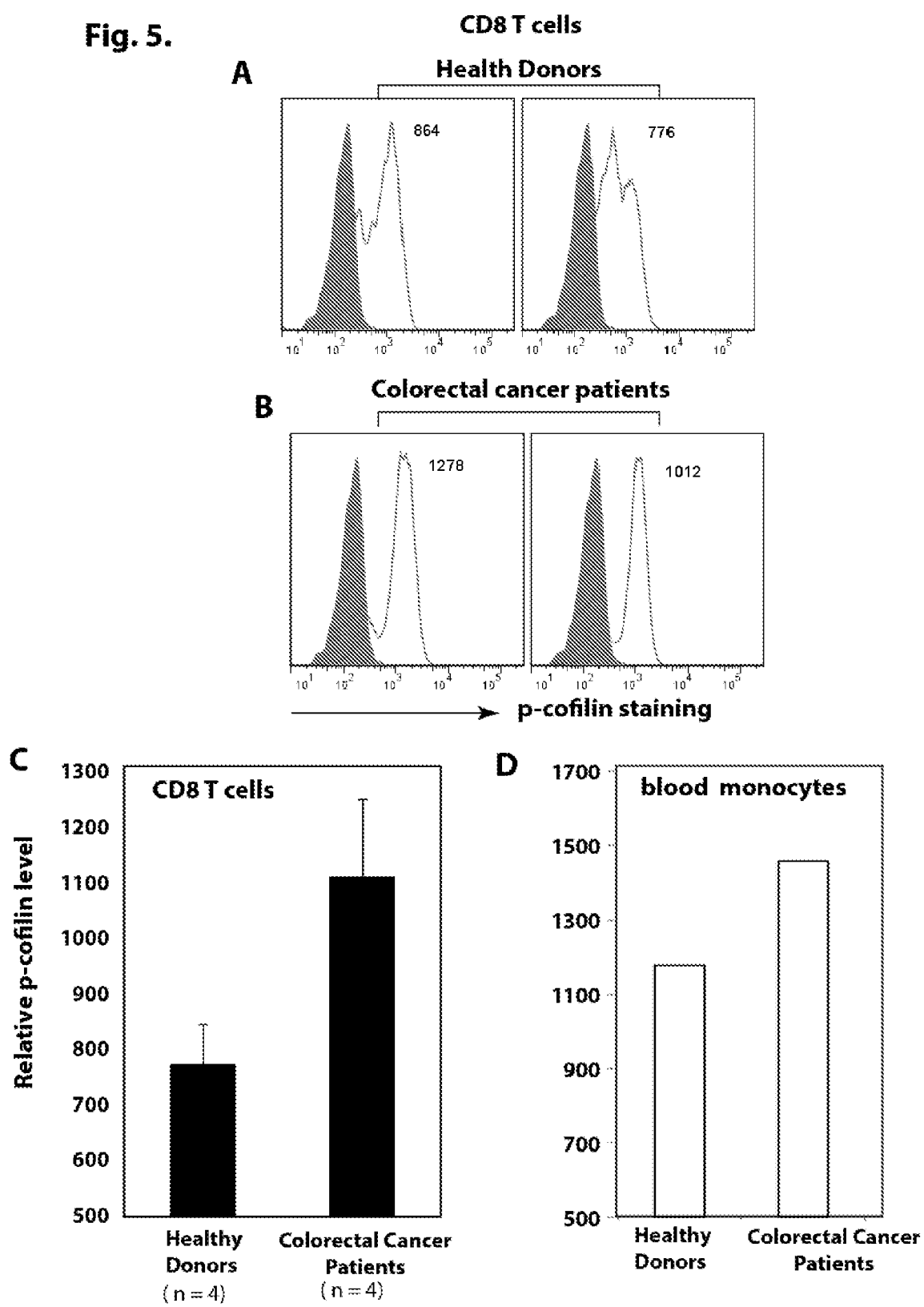
FIG. 5: Cofilin dysregulation in blood CD8 T cells and monocytes of cancer patients. Peripheral blood cytotoxic T cells (CD8 T cells) or monocytes from health donors or colorectal cancer patients were fixed, permeabilized, washed, and then stained with a rabbit polyclonal anti-human p-cofilin antibody for 60 min. Cells were washed twice and stained with Alexa Fluor 488-labeled anti-rabbit antibodies. Cells were washed twice, and then analyzed by flow cytometry. The relative p-cofilin staining was calculated. (A and B) shows the representative p-cofilin staining from 8 donors. The histogram plots of p-cofilin staining in CD8 T cells from 2 healthy donors (A) or from 2 colorectal cancer patients (B). The filled grey plots are isotype staining, the red line plots are p-cofilin staining. As shown, in cancer patients there is a narrowing of p-confilin staining, suggesting a decrease of CD8 T cell diversity and a CD8 T cell lineage polarization, which can cause T cell dysfunction and affects T cell mobility. (C) The relative P-cofilin staining was calculated by using the mean fluorescent intensity from p-cofilin staining. As shown, CD8 T cells from cancer patients (n=4 patients) have higher levels of p-cofilin staining than healthy donors (n=4 donors), an indication of cofilin inactivation. (D) P-cofilin was similarly analyzed in blood monocytes of cancer patients and healthy donors.

It was also found that in cancer patients, the CD8 T cells (cytotoxic T cells) and monocytes carry higher-levels of cofilin phosphorylation (FIGS. 5C and 5D), demonstrating that there is a cofilin dysregulation in T cells and other mononuclear cells of cancer patients, which can cause immune dysfunction and impair immune cell mobility. In addition, there is a narrowing of p-cofilin staining in the CD8 T cells of cancer patients (FIGS. 5A and B), suggesting a decrease in T cell diversity, and a tumor-driving T cell lineage polarization in cancers, which can cause T cell dysfunction and impair T cell mobility.

EXAMPLE

The following example is illustrative and non-limiting.

Example 1: Clinical Study

200 HIV-1 infected patients were enrolled. Among the HIV-infected patients, 98 had no previous or current ART at the time of the p-cofilin profiling, and 102 had ongoing ART for over a year, but 4 of the ART-treated patients had a viral load greater than 1,000 copies/ml and were excluded from the study for possible drug resistance. The CD4 T cell count and viral load of these subjects were measured every 3 months. One hundred age- and sex-matched healthy controls (HC) were enrolled. A summary of the subjects is listed in Table 1 and Table 2. Of the ART-naïve patients, 65 eventually received ART at around 6 months after the p-cofilin profiling, and were treated for more than a year. All of these patients receiving ART reached undetectable plasma HIV-1 RNA. ART-treated patients were further evaluated and categorized into immune responders (IR) and immune non-responders (INR). Both IR and INR were treated with ART for over one year. IRs were those who had a CD4 T cell recovery greater than 20% and a CD4 T cell count higher than 500 cells/μl; INRs had a CD4 T cell recovery less than 20% or a CD4 T cell count lower than 200 cells/μl. For isolating blood resting CD4 T cells from study subjects, peripheral blood mononuclear cells were freshly obtained from the subjects and purified by Ficoll-Hypaque density gradient centrifugation, followed by negative isolation of resting CD4 T cells as previously described (9, 57). Briefly, monoclonal antibodies against human CD14, CD56, HLA-DR, CD8, CD11b, and CD19 (BD Biosciences, San Jose, CA) were used. Antibody-bound cells were depleted using Dynabeads Pan Mouse IgG (Thermo Fisher Scientific). Purified cells were cultured in RPMI 1640 medium supplemented with 10% FBS. One million resting CD4 T cells from each blood donor were lysed in 40 μl SDS/T-PER extraction buffer [Novex Tris-Glycine SDS Sample Buffer, T-PER Tissue Protein Extraction Reagent (Thermo Fisher Scientific) and 2.5% 2-mercaptoethanol (Sigma-Aldrich)]. Cell lysates were heated at 100° C. for 8 minutes, immediately frozen and stored at −80° C., and then transported on dry ice to Theranostics Health (Gaithersburg, MD, USA) for p-cofilin reverse phase protein microarray analyses. A total of 296 coded cell lysates were printed onto the microarrays and profiled; 3 lysates did not generate readable signals and were excluded from data analyses.

Reverse Phase Protein Microarray (RPPA)

Cofilin reverse phase protein microarray printing and analyses of cell lysates were provided by Theranostics Health (Gaithersburg, MD, USA). Details of RPPA have been published previously (53). The RPPA directly couples the phospho-cofilin detection antibody with highly sensitive amplification systems that can yield detection sensitivities to fewer than 1,000 to 5,000 molecules per spot with good linearity (correlation coefficient or $R^2=0.990-0.999$) and inter-experiment precision ($R^2=0.973$). Published between-run and within-run analytical precision in our studies is a 3-13% CV (coefficient of variation) (58). The RPPA technology has been developed and optimized for performance as a fluorescence-based calibrated assay, generally identical in design and analysis to standard ELISA or standard clinical immunoassays. Each array consists of patient cell lysates printed in triplicate two-spot dilutions (neat and 1:4), high and low controls printed in triplicate two-spot dilutions (neat and 1:4), and 6-10 point calibrators. The analyte concentration is determined by extrapolation to a non-parametrically determined curve fit of the calibration curve and reported in relative fluorescence units. For data normalization, each protein analyte value (relative p-cofilin value) is normalized to the total amount of protein printed on that spot with a fluorescent stain (Sypro Ruby Blot Stain, Molecular Probes, Eugene OR) that binds to the amne group of proteins without bias. The protein loading value is also obtained by a calibrated assay technique. This total protein calibrator consists of a protein lysate with a known concentration, which upon dilution spans the linear dynamic range of protein concentration. Each sample value is then extrapolated to the calibrator. The quantified averages of the total protein levels from each test group are: HIV (n=98), 0.254; HIV+ART (n=95), 0.259; HC (healthy control, n=100), 0.252. There are no statistically significant differences in the total protein levels between the 3 groups (HC and HIV, p=0.77; HC and HIV+ART p=0.51; HIV and HIV+ART, p=0.64).

Purification of Resting CD4 T Subtypes from Peripheral Blood

Peripheral blood mononuclear cells (PBMC) were purified from peripheral blood of HIV-negative donors by centrifugation in Lymphocyte Separation Medium (Corning, Corning, NY), and resting CD4 T cells were further purified by two rounds of negative selection as previously described (9, 57). Briefly, for the first-round depletion, monoclonal antibodies against human CD14, CD56 and HLA-DR, DP, and DQ (BD Biosciences, San Jose, CA) were used. For the second-round depletion, monoclonal antibodies against human CD8, CD11b, and CD19 (BD Biosciences, San Jose, CA) were used. Antibody-bound cells were depleted using Dynabeads Pan Mouse IgG (Invitrogen, Carlsbad, CA). For further negative selection of the memory and naïve CD4 T cell subsets, monoclonal antibody against either CD45RA (0.02 μl per million cells) or CD45RO (0.1 μl per million cells) (BD Biosciences, San Jose, CA) was added during the second round of depletion. Purified cells were cultured in RPMI-1640 medium supplemented with 10% heat-inactivated fetal bovine serum (Invitrogen, Carlsbad, CA), penicillin (50 U/ml) (Invitrogen, Carlsbad, CA), and streptomycin (50 μg/ml) (Invitrogen, Carlsbad, CA). Cells were rested overnight before infection or treatment. For α4β7 surface receptor upregulation, resting CD4 T cells were also cultured in IL-7 (5 ng/ml) for 3 days.

Western Blotting for p-Cofilin and Cofilin

One million cells were lysed in NuPAGE LDS Sample Buffer (Invitrogen, Carlsbad, CA) followed by sonication. Samples were heated at 70° C. for 10 minutes, separated by SDS-PAGE, and then transferred onto nitrocellulose membranes (Invitrogen, Carlsbad, CA). The membranes were washed in TBST for 3 minutes and then blocked for 30 minutes at room temperature with 5% milk. The blots were incubated with a mouse anti-cofilin antibody (1:1000 dilution) (BD Biosciences, San Jose, CA) and a rabbit anti-phospho-cofilin (ser3) antibody (1:500 dilution) (Cell Signaling) diluted in 3% milk-TBST and rocked overnight at 4° C. The blots were washed three times for 15 minutes, then incubated with DyLight 680 goat anti-mouse and DyLight 800 goat anti-rabbit antibodies (KPL, Gaithersburg, MD) (1:5000 diluted in blocking buffer) for 1 hour at 4° C. The blots were washed three times for 15 minutes and scanned with Odyssey Infrared Imager (Li-cor Biosciences).

Chemotaxis Assay

A half million cells were resuspended into 100 μl RPMI-1640 medium and then added to the upper chamber of a 24-well transwell plate (Corning, Corning, NY). The lower chamber was filled with 600 μl of medium premixed with CXCL12 (40 ng/ml). The plate was incubated at 37° C. for 2 hours, and then the upper chamber was removed and cells in the lower chamber were counted. To ensure accurate enumeration of cells, only Z2 Coulter Particle Count and Size Analyzer (Beckman Coulter) was used. Where indicated, different concentrations of R10015 (55) or DMSO were added to cell culture, incubated for 1 hour at 37° C. before adding cells to the upper chamber. Cells were also treated with the anti-human α4β7 integrin antibody (Act-1) or the control mouse IgG1 antibody for 15 minutes before adding cells to the upper chamber. Act-1 was also added to the lower chamber (1 μg/ml) with CXCL12 (40 ng/ml). Multiple donors were used for chemotaxis assay.

Intracellular p-Cofilin Staining and Flow Cytometry

One million cells were fixed, permeabilized with methanol, washed, and then stained with an anti-human p-cofilin antibody using an intracellular protein staining kit (Virongy, Manassas, V) for 60 min at room temperature. Cells were washed twice and stained with Alexa Fluor 488-labeled chicken anti-rabbit antibodies (Invitrogen, Carlsbad, CA). Cells were washed twice, and then analyzed on a FACSCalibur (BD Biosciences, San Jose, CA).

Statistical Analysis

Statistical calculations were performed using IBM SPSS statistics 23. Categorical data were described and analyzed by frequency and chi-square ($\chi^2$) test. For parametric comparison, two-tailed Mann-Whitney U test was used to assess differences between groups during p-cofilin profiling (FIG. 2). Spearman rank correlations tests were used to measure the correlations between variables. Unless otherwise stated, p value less than 0.05 was considered as statistically significant.

REFERENCES

1. Deeks S G, Kitchen C M, Liu L, Guo H, Gascon R, Narvaez A B, Hunt P, Martin J N, Kahn J O, Levy J, McGrath M S, Hecht F M. Immune activation set point during early HIV infection predicts subsequent CD4+ T-cell changes independent of viral load. Blood. 2004; 104(4):942-7. PubMed PMID: 15117761.
2. Cecchinato V, Bernasconi E, Speck R F, Proietti M, Sauermann U, D'Agostino G, Danelon G, Rezzonico Jost T, Grassi F, Raeli L, Schoni-Affolter F, Stahl-Hennig C, Uguccioni M, Swiss HIVCS. Impairment of CCR6+ and CXCR3+Th Cell Migration in HIV-1 Infection Is Rescued by Modulating Actin Polymerization. J Immunol. 2017; 198(1):184-95. doi: 10.4049/jimmunol.1600568. PubMed PMID: 27895171; PMCID: PMC5164881.
3. Mavigner M, Cazabat M, Dubois M, L'Faqihi F E, Requena M, Pasquier C, Klopp P, Amar J, Alric L, Barange K, Vinel J P, Marchou B, Massip P, Izopet J, Delobel P. Altered CD4+ T cell homing to the gut impairs mucosal immune reconstitution in treated HIV-infected individuals. J Clin Invest. 2012; 122(1):62-9. doi: 10.1172/JCI59011. PubMed PMID: 22156200; PMCID: PMC3248296.
4. Perez-Patrigeon S, Vingert B, Lambotte O, Viard J P, Delfraissy J F, Theze J, Chakrabarti L A. HIV infection impairs CCR7-dependent T-cell chemotaxis independent of CCR7 expression. Aids. 2009; 23(10):1197-207. PubMed PMID: 19455014.
5. Ryan E S, Micci L, Fromentin R, Paganini S, McGary C S, Easley K, Chomont N, Paiardini M. Loss of Function of Intestinal IL-17 and IL-22 Producing Cells Contributes to Inflammation and Viral Persistence in SIV-Infected Rhesus Macaques. PLoS Pathog. 2016; 12(2):e1005412. doi: 10.1371/journal.ppat.1005412. PubMed PMID: 26829644; PMCID: PMC4735119.
6. Cecchinato V, Trindade C J, Laurence A, Heraud J M, Brenchley J M, Ferrari M G, Zaffiri L, Tryniszewska E, Tsai W P, Vaccari M, Parks R W, Venzon D, Douek D C, O'Shea J J, Franchini G. Altered balance between Th17 and Th1 cells at mucosal sites predicts AIDS progression in simian immunodeficiency virus-infected macaques. Mucosal Immunol. 2008; 1(4):279-88. doi: 10.1038/mi.2008.14. PubMed PMID: 19079189; PMCID: PMC2997489.
7. Byrareddy S N, Arthos J, Cicala C, Villinger F, Ortiz K T, Little D, Sidell N, Kane M A, Yu J, Jones J W, Santangelo P J, Zurla C, McKinnon L R, Arnold K B, Woody C E, Walter L, Roos C, Noll A, Van Ryk D, Jelicic K, Cimbro R, Gumber S, Reid M D, Adsay V, Amancha P K, Mayne A E, Parslow T G, Fauci A S, Ansari A A. Sustained virologic control in SIV+ macaques after antiretroviral and alpha4beta7 antibody therapy. Science. 2016; 354 (6309):197-202. doi: 10.1126/science.aag1276. PubMed PMID: 27738167; PMCID: PMC5405455.
8. Finzi D, Hermankova M, Pierson T, Carruth L M, Buck C, Chaisson R E, Quinn T C, Chadwick K, Margolick J, Brookmeyer R, Gallant J, Markowitz M, Ho D D, Richman D D, Siliciano R F. Identification of a reservoir for HIV-1 in patients on highly active antiretroviral therapy. Science. 1997; 278(5341):1295-300.
9. Yoder A, Yu D, Dong L, Iyer S R, Xu X, Kelly J, Liu J, Wang W, Vorster P J, Agulto L, Stephany D A, Cooper J N, Marsh J W, Wu Y. HIV envelope-CXCR4 signaling activates cofilin to overcome cortical actin restriction in resting CD4 T cells. Cell. 2008; 134(5):782-92. PubMed PMID: 18775311.
10. Wu Y, Yoder A. Chemokine coreceptor signaling in HIV-1 infection and pathogenesis. PLoS Pathog. 2009; 5(12):e1000520. PubMed PMID: 20041213.
11. Lanitis E, Dangaj D, Irving M, Coukos G. Mechanisms regulating T-cell infiltration and activity in solid tumors. Ann Oncol. 2017; 28(suppl_12):xii18-xii32. doi: 10.1093/annonc/mdx238. PubMed PMID: 29045511.
12. Feng Y, Broder C C, Kennedy P E, Berger E A. HIV-1 entry cofactor: functional cDNA cloning of a seven-transmembrane, G protein-coupled receptor. Science. 1996; 272(5263):872-7. PubMed PMID: 8629022.
13. Alkhatib G, Combadiere C, Broder C C, Feng Y, Kennedy P E, Murphy P M, Berger E A. CC CKR5: a RANTES, MIP-1alpha, MIP-1beta receptor as a fusion cofactor for macrophage-tropic HIV-1. Science. 1996; 272(5270):1955-8. PubMed PMID: 8658171.
14. Weissman D, Rabin R L, Arthos J, Rubbert A, Dybul M, Swofford R, Venkatesan S, Farber J M, Fauci A S. Macrophage-tropic HIV and SIV envelope proteins induce a signal through the CCR5 chemokine receptor. Nature. 1997; 389(6654):981-5.
15. Schweneker M, Favre D, Martin J N, Deeks S G, McCune J M. HIV-induced changes in T cell signaling pathways. J Immunol. 2008; 180(10):6490-500. PubMed PMID: 18453567; PMCID: PMC2648824.
16. Cameron P U, Saleh S, Sallmann G, Solomon A, Wightman F, Evans V A, Boucher G, Haddad E K, Sekaly R P, Harman A N, Anderson J L, Jones K L, Mak J, Cunningham A L, Jaworowski A, Lewin S R. Establishment of HIV-1 latency in resting CD4+ T cells depends on chemokine-induced changes in the actin cytoskeleton. Proc Natl Acad Sci USA. 2010; 107(39):16934-9. PubMed PMID: 20837531.
17. Wang Z, Shang H, Jiang Y. Chemokines and Chemokine Receptors: Accomplices for Human Immunodeficiency Virus Infection and Latency. Front Immunol. 2017; 8:1274. doi: 10.3389/fimmu.2017.01274. PubMed PMID: 29085362; PMCID: PMC5650658.
18. Wang Z, Wu T, Ma M, Zhang Z, Fu Y, Liu J, Xu J, Ding H, Han X, Chu Z, Wu Y, Shang H, Jiang Y. Elevated interferon-gamma-induced protein 10 and its receptor CXCR3 impair N K cell function during HIV infection. J Leukoc Biol. 2017; 102(1):163-70. doi: 10.1189/jlb.5A1016-444R. PubMed PMID: 28465448.

19. Bamburg J R, Harris H E, Weeds A G. Partial purification and characterization of an actin depolymerizing factor from brain. FEBS Lett. 1980; 121(1):178-82. PubMed PMID: 6893966.
20. Bamburg J R. Proteins of the ADF/cofilin family: essential regulators of actin dynamics. Annu Rev Cell Dev Biol. 1999; 15:185-230. PubMed PMID: 10611961.
21. Pope B J, Zierler-Gould K M, Kuhne R, Weeds A G, Ball U. Solution structure of human cofilin: actin binding, pH sensitivity, and relationship to actin-depolymerizing factor. J Biol Chem. 2004; 279(6):4840-8. PubMed PMID: 14627701.
22. Pavlov D, Muhlrad A, Cooper J, Wear M, Reisler E. Actin filament severing by cofilin. J Mol Biol. 2007; 365(5):1350-8. PubMed PMID: 17134718.
23. Carlier M F, Laurent V, Santolini J, Melki R, Didry D, Xia G X, Hong Y, Chua N H, Pantaloni D. Actin depolymerizing factor (ADF/cofilin) enhances the rate of filament turnover: implication in actin-based motility. J Cell Biol. 1997; 136(6):1307-22. PubMed PMID: 9087445.
24. Galkin V E, Orlova A, VanLoock M S, Shvetsov A, Reisler E, Egelman E H. ADF/cofilin use an intrinsic mode of F-actin instability to disrupt actin filaments. J Cell Biol. 2003; 163(5):1057-66. PubMed PMID: 14657234.
25. Pollard T D, Borisy G G. Cellular motility driven by assembly and disassembly of actin filaments. Cell. 2003; 112(4):453-65. PubMed PMID: 12600310.
26. McGough A, Pope B, Chiu W, Weeds A. Cofilin changes the twist of F-actin: implications for actin filament dynamics and cellular function. J Cell Biol. 1997; 138(4):771-81. PubMed PMID: 9265645.
27. Yang N, Higuchi O, Ohashi K, Nagata K, Wada A, Kangawa K, Nishida E, Mizuno K. Cofilin phosphorylation by LIM-kinase 1 and its role in Rac-mediated actin reorganization. Nature. 1998; 393(6687):809-12. PubMed PMID: 9655398.
28. Ambach A, Saunus J, Konstandin M, Wesselborg S, Meuer S C, Samstag Y. The serine phosphatases PP1 and PP2A associate with and activate the actin-binding protein cofilin in human T lymphocytes. Eur J Immunol. 2000; 30(12):3422-31. PubMed PMID: 11093160.
29. Niwa R, Nagata-Ohashi K, Takeichi M, Mizuno K, Uemura T. Control of actin reorganization by Slingshot, a family of phosphatases that dephosphorylate ADF/cofilin. Cell. 2002; 108(2):233-46. PubMed PMID: 11832213.
30. Gohla A, Birkenfeld J, Bokoch G M. Chronophin, a novel HAD-type serine protein phosphatase, regulates cofilin-dependent actin dynamics. Nat Cell Biol. 2005; 7(1):21-9. PubMed PMID: 15580268.
31. Yoo Y, Ho H J, Wang C, Guan J L. Tyrosine phosphorylation of cofilin at Y68 by v-Src leads to its degradation through ubiquitin-proteasome pathway. Oncogene. 29(2): 263-72. PubMed PMID: 19802004.
32. Bernstein B W, Bamburg J R. ADF/cofilin: a functional node in cell biology. Trends Cell Biol. 2010; 20(4):187-95. PubMed PMID: 20133134.
33. Andrianantoandro E, Pollard T D. Mechanism of actin filament turnover by severing and nucleation at different concentrations of ADF/cofilin. Mol Cell. 2006; 24(1):13-23. PubMed PMID: 17018289.
34. Chan C, Beltzner C C, Pollard T D. Cofilin dissociates Arp2/3 complex and branches from actin filaments. Curr Biol. 2009; 19(7):537-45. PubMed PMID: 19362000.
35. Cairns B R, Erdjument-Bromage H, Tempst P, Winston F, Kornberg R D. Two actin-related proteins are shared functional components of the chromatin-remodeling complexes RSC and SWI/SNF. Mol Cell. 1998; 2(5):639-51. PubMed PMID: 9844636.
36. Zhao K, Wang W, Rando O J, Xue Y, Swiderek K, Kuo A, Crabtree G R. Rapid and phosphoinositol-dependent binding of the SWI/SNF-like BAF complex to chromatin after T lymphocyte receptor signaling. Cell. 1998; 95(5): 625-36. PubMed PMID: 9845365.
37. Hofmann W A, Stojiljkovic L, Fuchsova B, Vargas G M, Mavrommatis E, Philimonenko V, Kysela K, Goodrich J A, Lessard J L, Hope T J, Hozak P, de Lanerolle P. Actin is part of pre-initiation complexes and is necessary for transcription by RNA polymerase I I. Nat Cell Biol. 2004; 6(11):1094-101. PubMed PMID: 15502823.
38. Han L, Stope M B, de Jesus M L, Oude Weernink P A, Urban M, Wieland T, Rosskopf D, Mizuno K, Jakobs K H, Schmidt M. Direct stimulation of receptor-controlled phospholipase D1 by phospho-cofilin. Embo J. 2007; 26(19):4189-202. PubMed PMID: 17853892.
39. Eibert S M, Lee K H, Pipkorn R, Sester U, Wabnitz G H, Giese T, Meuer S C, Samstag Y. Cofilin peptide homologs interfere with immunological synapse formation and T cell activation. Proc Natl Acad Sci USA. 2004; 101(7):1957-62. PubMed PMID: 14762171.
40. Samstag Y, Eibert S M, Klemke M, Wabnitz G H. Actin cytoskeletal dynamics in T lymphocyte activation and migration. J Leukoc Biol. 2003; 73(1):30-48. PubMed PMID: 12525560.
41. Samstag Y, Nebl G. Ras initiates phosphatidyl-inositol-3-kinase (PI3K)/PKB mediated signalling pathways in untransformed human peripheral blood T lymphocytes. Adv Enzyme Regul. 2005; 45:52-62. PubMed PMID: 16083947.
42. Vorster P J, Guo J, Yoder A, Wang W, Zheng Y, Xu X, Yu D, Spear M, Wu Y. LIM kinase 1 modulates cortical actin and CXCR4 cycling and is activated by HIV-1 to initiate viral infection. J Biol Chem. 2011; 286(14): 12554-64. PubMed PMID: 21321123.
43. Saleh S, Solomon A, Wightman F, Xhilaga M, Cameron P U, Lewin S R. CCR7 ligands CCL19 and CCL21 increase permissiveness of resting memory CD4+ T cells to HIV-1 infection: a novel model of HIV-1 latency. Blood. 2007; 110(13):4161-4. PubMed PMID: 17881634.
44. Guo J, Wang W, Yu D, Wu Y. Spinoculation triggers dynamic actin and cofilin activity facilitating HIV-1 infection of transformed and resting CD4 T cells. J Virol. 2011; 85(19):9824-33. PubMed PMID: 21795326.
45. Jimenez-Baranda S, Gomez-Mouton C, Rojas A, Martinez-Prats L, Mira E, Ana Lacalle R, Valencia A, Dimitrov D S, Viola A, Delgado R, Martinez A C, Manes S. Filamin-A regulates actin-dependent clustering of HIV receptors. Nat Cell Biol. 2007; 9(7):838-46. PubMed PMID: 17572668.
46. Trushin S A, Bren G D, Badley A D. CXCR4 Tropic HIV-1 gp120 Inhibition of SDF-1alpha-Induced Chemotaxis Requires Lck and is Associated with Cofilin Phosphorylation. Open Virol J. 2010; 4:157-62. PubMed PMID: 20835359.
47. Stolp B, Reichman-Fried M, Abraham L, Pan X, Giese S I, Hannemann S, Goulimari P, Raz E, Grosse R, Fackler O T. HIV-1 Nef interferes with host cell motility by deregulation of Cofilin. Cell Host Microbe. 2009; 6(2): 174-86. PubMed PMID: 19683683.
48. Nobile C, Rudnicka D, Hasan M, Aulner N, Porrot F, Machu C, Renaud O, Prevost M C, Hivroz C, Schwartz O, Sol-Foulon N. HIV-1 Nef inhibits ruffles, induces filopodia, and modulates migration of infected lymphocytes. J Virol. 2010; 84(5):2282-93. PubMed PMID: 20015995.
49. He S, Fu Y, Guo J, Spear M, Yang J, Trinite B, Qin C, Fu S, Jiang Y, Zhang Z, Xu J, Ding H, Levy D N, Chen W, Petricoin E, 3rd, Liotta L A, Shang H, Wu Y. Cofilin hyperactivation in HIV infection and targeting the cofilin pathway using an anti-alpha4beta7 integrin antibody. Sci Adv. 2019; 5(1):eaat7911. doi: 10.1126/sciadv.aat7911. PubMed PMID: 30662943; PMCID: PMC6326757.
50. Wu Y, Yoder A, Yu D, Wang W, Liu J, Barrett T, Wheeler D, Schlauch K. Cofilin activation in peripheral CD4 T cells of HIV-1 infected patients: a pilot study. Retrovirology. 2008; 5:95. PubMed PMID: 18928553.
51. Santosuosso M, Righi E, Lindstrom V, Leblanc P R, Poznansky M C. HIV-1 envelope protein gp120 is present at high concentrations in secondary lymphoid organs of individuals with chronic HIV-1 infection. J Infect Dis. 2009; 200(7):1050-3. PubMed PMID: 19698075.
52. Ramratnam B, Mittler J E, Zhang L, Boden D, Hurley A, Fang F, Macken C A, Perelson A S, Markowitz M, Ho D D. The decay of the latent reservoir of replication-competent HIV-1 is inversely correlated with the extent of residual viral replication during prolonged anti-retroviral therapy. Nat Med. 2000; 6(1):82-5. PubMed PMID: 10613829.
53. Pierobon M, Belluco C, Liotta L A, Petricoin E F, 3rd. Reverse phase protein microarrays for clinical applications. Methods Mol Biol. 2011; 785:3-12. PubMed PMID: 21901589.
54. Lappalainen P, Drubin D G. Cofilin promotes rapid actin filament turnover in vivo. Nature. 1997; 388(6637):78-82. PubMed PMID: 9214506.
55. Yi F, Guo J, Dabbagh D, Spear M, He S, Kehn-Hall K, Fontenot J, Yin Y, Bibian M, Park C M, Zheng K, Park H, Soloveva V, Gharaibeh D, Retterer C, Zamani R, Pitt M L, Naughton J, Jiang Y, Shang H, Hakami R M, Ling B, Young J A, Bavari S, Xu X, Feng Y, Wu Y. Discovery of Novel Small Molecule Inhibitors of LIM Domain Kinase for Inhibiting HIV-1. J Virol. 2017. doi: 10.1128/JVI.02418-16. PubMed PMID: 28381571.
56. Nishita M, Aizawa H, Mizuno K. Stromal cell-derived factor 1alpha activates LIM kinase 1 and induces cofilin phosphorylation for T-cell chemotaxis. Molecular & Cellular Biology. 2002; 22(3):774-83.
57. Wu Y, Marsh J W. Selective transcription and modulation of resting T cell activity by preintegrated HIV DNA. Science. 2001; 293(5534):1503-6.
58. Wulfkuhle J D, Berg D, Wolff C, Langer R, Tran K, Illi J, Espina V, Pierobon M, Deng J, DeMichele A, Walch A, Bronger H, Becker I, Waldhor C, Hofler H, Esserman L, Investigators IST, Liotta L A, Becker K F, Petricoin E F, 3rd. Molecular analysis of HER2 signaling in human breast cancer by functional protein pathway activation mapping. Clin Cancer Res. 2012; 18(23):6426-35. doi: 10.1158/1078-0432.CCR-12-0452. PubMed PMID: 23045247.

What is claimed is:

1. A method for treating cancer in a patient, comprising
   (a) quantifying cofilin phosphorylation levels in one or more cells chosen from helper CD4+ T cells, cytotoxic CD8+ T cells, B cells, and/or natural killer cells, of said patient, wherein said patient has lower or higher cofilin phosphorylation levels than a control healthy person; and
   (b) administering to said patient an effective amount of a composition that restores cofilin phosphorylation.

2. The method of claim 1, wherein said composition comprises okadaic acid.

* * * * *